US00PP22128P2

(12) United States Plant Patent
Yandall et al.

(10) Patent No.: US PP22,128 P2
(45) Date of Patent: Sep. 6, 2011

(54) ***OPHIOPOGON* PLANT NAMED 'YAPARD'**

(50) Latin Name: *Ophiopogon planiscapus*
Varietal Denomination: Yapard

(76) Inventors: Stephen Yandall, Penzance (GB); Susan Yandall, Penzance (GB)

( * ) Notice: Subject to any disclaimer, the term of this patent is extended or adjusted under 35 U.S.C. 154(b) by 36 days.

(21) Appl. No.: 12/653,420

(22) Filed: Dec. 14, 2009

(51) Int. Cl.
*A01H 5/00* (2006.01)

(52) U.S. Cl. ..... Plt./384

(58) Field of Classification Search ..... Plt./384, Plt./263.1, 373
See application file for complete search history.

*Primary Examiner* — Kent L Bell
(74) *Attorney, Agent, or Firm* — Penny J. Aguirre

(57) ABSTRACT

A new cultivar of *Ophiopogon,* 'YAPARD', characterized by its long and wide dark grey-green to dark grey-purple colored foliage, its abundance of flowers, and its vigorous growth habit with a high rate of adventitious root development.

2 Drawing Sheets

Botanical classification: *Ophiopogon planiscapus.*
Varietal denomination: 'YAPARD'.

BACKGROUND OF THE INVENTION

The present invention relates to a new and distinct cultivar of *Ophiopogon planiscapus* (Nigrescens type) and will be referred to hereafter by its cultivar name, 'YAPARD'. 'YAPARD' is a new cultivar of mondo grass and is a grass-like perennial grown for use in border, and containers, and as groundcovers.

The new variety of *Ophiopogon* is the result of an ongoing breeding program by the Inventors in Penzance, Cornwall, United Kingdom that commenced in 1980. The goal of the breeding program is to produce new cultivars of *Ophiopogon* with increased vigor, larger leaves, longer flower spikes, and suitability as a groundcover.

The new variety of *Ophiopogon,* 'YAPARD', arose from a cross made in 2002 between unnamed proprietary seedlings developed of the Inventors as both the male and female parents. 'YAPARD' was selected as a single unique plant in summer of 2005.

Asexual reproduction of the new cultivar was first accomplished by in vitro propagation under the direction of the Inventors in Stoneyford, Co. Kilkenny, Republic of Ireland in summer of 2005. The characteristics of this cultivar have been determined both by division and in vitro propagation to be stable and to reproduce true to type in successive generations.

SUMMARY OF THE INVENTION

The following traits have been repeatedly observed and represent the characteristics of the new cultivar as observed for a period of 4 years in Penzance, Cornwall, United Kingdom. These attributes in combination distinguish 'YAPARD' from all other selections of *Ophiopogon* known to the Inventors.

1. 'YAPARD' exhibits dark grey-green to grey-purple colored foliage.
2. 'YAPARD' exhibits foliage that is wide and long.
3. 'YAPARD' exhibits an abundance of flowers.
4. 'YAPARD' exhibits a vigorous growth habit with a high rate of adventitious root development.

'YAPARD' can be compared to its parent plants. The female parent differs from 'YAPARD' in being less floriferous and in having a slower growth rate. The male parent differs from 'YAPARD' in having shorter flower stems, smaller flowers, and in having a slightly slower growth rate. 'YAPARD' can be compared to the cultivar 'Nigrescens' (not patented), which has similar foliage coloration to 'YAPARD'. 'Nigrescens' differs from 'YAPARD' in having narrower and shorter foliage, less flowers, a slower growth rate and slower adventitious root development. There are no other close comparison plants for 'YAPARD' known to the Inventors.

BRIEF DESCRIPTION OF THE DRAWING

The accompanying colored photographs illustrate the overall appearance and distinct characteristics of the new *Ophiopogon.*

The photographs in FIG. 1 and FIG. 2 were taken of 3 year-old plants as grown in a 3-liter container garden in Penzance, Cornwall, United Kingdom.

Figure 1:
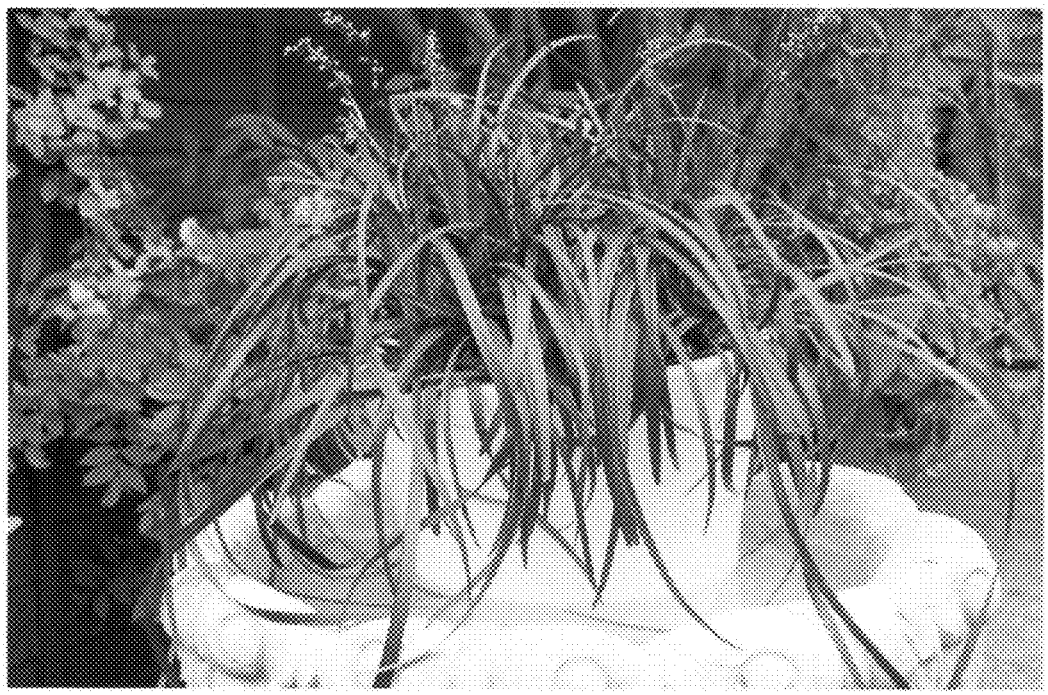

The photograph in FIG. 1 illustrates the plant habit and appearance of plants of 'YAPARD' in bloom in mid summer.

Figure 2:
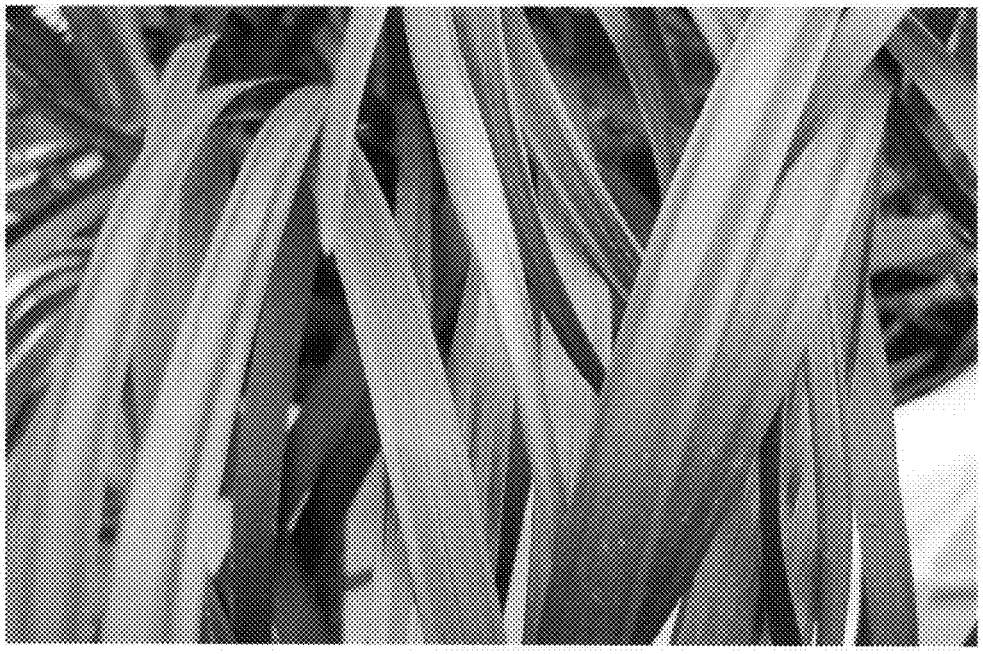

The photograph in FIG. 2 provides a close-up view of the foliage of 'YAPARD'.

The colors in the photograph may differ slightly from the color values cited in the detailed botanical description, which accurately describe the colors of the new *Ophiopogon.*

DETAILED BOTANICAL DESCRIPTION

The following botanical description describes 3 year-old plants of 'YAPARD' as grown outdoors in 3-liter containers in Penzance, Cornwall, United Kingdom. The new *Ophiopogon* has not been observed under all possible environmental conditions. The phenotype may vary somewhat with variations in temperature, day-length, light intensity, soil types, and water and fertility levels without, however, any variance in genotype. The color determinations are in accordance with The 2007 R.H.S. Colour Chart of The Royal Horticultural Society, London, England, except where general color terms of ordinary dictionary significance are used.

General description:

*Blooming habit.*—July to August in southern United Kingdom.

*Plant habit.*—Herbaceous, clump-forming and slowly spreading into a groundcover.

*Height and spread.*—About 60 cm in height and 60 cm in spread in 3 years (to end of foliage).

*Cold hardiness.*—At least to −18° C., has not been tested at colder temperatures.

*Diseases and Pests.*—No unique aspects concerning susceptibility or resistance to diseases or pests has been observed.

*Root description.*—Deep penetrating roots and finer feeder roots from crown, high rate of adventitious root development.

*Branching.*—Stem-less, leaves arise from base.

Growth and propagation:

*Propagation.*—Tissue culture preferred, division is also possible.

*Root development.*—About 40 weeks from a plug to fully develop in a 1-liter container.

*Growth rate.*—Vigorous (up to 50% more vigorous than 'Nigrescens').

*Offshoot production.*—Approximately 20 offshoots are produced in one growing season from a single shoot, a four year old plant typically has 4 times the increase in shoots in comparison to Nigrescens'.

Foliage description:

*Leaf shape.*—Linear.

*Leaf division.*—Simple.

*Leaf base.*—Truncate to rootstock.

*Leaf apex.*—Acute.

*Leaf aspect.*—Leaves initially emerge upright, then arch and curl when mature.

*Leaf venation.*—Parallel, not prominent or conspicuous, color matches leaf color.

*Leaf margins.*—Entire.

*Leaf attachment and arrangement.*—Sessile, arise in tufts from rootstock.

*Leaf size.*—7 to 8 mm in width (at midpoint) and up to 40 cm in length.

*Leaf number.*—Average of 20 per rootstock (shoot) with average of 25 shoots per 3-liter container.

*Leaf surface.*—Glabrous on upper and lower surface.

*Leaf color.*—Emerging foliage upper surface; 144C at base becoming 146A in mid region and N186A tinged with 146A at apex, emerging leaves lower surface; 150D at base becoming 143C in mid region and N186A at apex, mature foliage upper and lower surface; N186A tinged with 146A.

Flower description:

*Inflorescence type.*—An upright held raceme comprised of 2 to 3 campanulate shaped flowers arranged in whorls on the upper portion of the scape.

*Inflorescence size.*—Reaches up to 7 cm in height and about 2 cm in width (excluding peduncle).

*Flower fragrance.*—Present.

*Flower quantity.*—Average of 35 per inflorescence, persistent.

*Flower lastingness.*—An average of 12 days per flower, with each raceme blooming for about 3 weeks.

*Flower buds.*—Ovoid in shape, average of 5 mm in diameter and 7 mm in length, 86D in color.

*Flower aspect.*—Held horizontally to about 45° angle from scape.

*Flower shape.*—Campanulate.

*Flower size.*—About 10 mm in depth and 9 mm in diameter.

*Tepals.*—6 (2 rows of 3), ovate in shape, margin is entire, apex is rounded, fused at base, upper and lower surface is glabrous and smooth, thick and fleshy texture, color of outer surface is 85A and 86D in center portion blending to 85C at margin, color of inner surface is NN155D, inner tepals are about 6 mm in length and 3.5 mm in width, outer tepals are about 5 mm in length and 2 mm in width.

*Bracteole.*—Linear in shape, attenuate apex, truncate base, an average of 11 mm in length and 1 mm in width, 186A in color, surface is glabrous.

*Peduncles.*—Flattened, narrowly winged (<1 mm in width) on each side, solid, about 20 cm in length (from base of plant to lowest flower) and 1 to 3 mm in width, held erect, strong, color is N186B with shading of 146D and 150D at base, surface is glabrous.

*Pedicels.*—An average of 2 mm in length and <1 mm in width, 186A in color, surface is glabrous.

Reproductive organs:

*Gynoecium.*—1 Pistil, stigma is pointed in shape, about 0.5 mm in length and width, and NN155D and sometimes flushed with 85C in color, style is cylindrical and tapering at apex, about 4 mm in length and 1 mm in width (at base) and NN155D and sometimes flushed with 85C in color, ovary is partly inferior, globose in shape, about 2.5 mm in diameter and NN155D in color.

*Androcoecium.*—6 stamens, joined to base of tepals, anthers are about 2 mm in length, 0.5 mm in width and 158A flushed with 85C in color, filaments are about 0.5 mm in length and 155A in color, pollen is moderate in quantity and 158A in color.

*Fruit and seed.*—Berry; present for about 3 weeks in fall, globose in shape, 6 to 8 mm in diameter, N186B in color and 145A and 145B when shaded, seed; 1 per berry, round in shape, an average of 5 mm in diameter, fleshy, N155B in color.

It is claimed:

1. A new and distinct cultivar of *Ophiopogon* plant named 'YAPARD' as herein illustrated and described.

* * * * *